United States Patent
Dal Farra et al.

(10) Patent No.: US 8,722,627 B2
(45) Date of Patent: *May 13, 2014

(54) PROTEASOME-ACTIVATING LIGHTENING PEPTIDIC HYDROLYZATES AND COMPOSITIONS CONTAINING THEM

(75) Inventors: Claude Dal Farra, Kerhonkson, NY (US); Nouha Domloge, Valbonne (FR); Jean-Marie Botto, Valbonne (FR)

(73) Assignee: ISP Investments Inc., Wilmington, DE (US)

( * ) Notice: Subject to any disclaimer, the term of this patent is extended or adjusted under 35 U.S.C. 154(b) by 111 days.

This patent is subject to a terminal disclaimer.

(21) Appl. No.: 13/265,034

(22) PCT Filed: Apr. 22, 2010

(86) PCT No.: PCT/FR2010/000325
§ 371 (c)(1),
(2), (4) Date: Oct. 18, 2011

(87) PCT Pub. No.: WO2010/122245
PCT Pub. Date: Oct. 28, 2010

(65) Prior Publication Data
US 2012/0100086 A1    Apr. 26, 2012

(30) Foreign Application Priority Data
Apr. 23, 2009 (FR) .................... 09 01979

(51) Int. Cl.
*A61K 8/64* (2006.01)
*A61K 38/08* (2006.01)
*A61K 38/07* (2006.01)
*A61K 38/06* (2006.01)
*C07K 5/08* (2006.01)
*C07K 5/10* (2006.01)
*C07K 7/00* (2006.01)
*C07K 7/06* (2006.01)
*A61Q 19/08* (2006.01)
*A61Q 19/00* (2006.01)
*A61Q 19/02* (2006.01)
*C07K 5/093* (2006.01)
*C07K 5/113* (2006.01)
*A61K 9/00* (2006.01)

(52) U.S. Cl.
CPC ............... *C07K 5/08* (2013.01); *C07K 5/0819* (2013.01); *C07K 5/10* (2013.01); *C07K 5/1021* (2013.01); *C07K 7/06* (2013.01); *C07K 7/00* (2013.01); *A61Q 19/08* (2013.01); *A61Q 19/00* (2013.01); *A61Q 19/004* (2013.01); *A61Q 19/02* (2013.01); *A61K 8/64* (2013.01); *A61K 8/645* (2013.01); *A61K 38/08* (2013.01); *A61K 38/07* (2013.01); *A61K 38/06* (2013.01); *A61K 9/0014* (2013.01)

USPC ....... 514/18.8; 514/18.6; 514/21.9; 514/21.8; 530/330; 530/331; 424/59; 424/70.14

(58) Field of Classification Search
CPC ............... C07K 7/00; C07K 7/04; C07K 7/06; C07K 5/08; C07K 5/10; C07K 5/0819; C07K 5/1021; A61Q 19/08; A61Q 19/00; A61Q 19/004; A61Q 19/02; A61K 38/06; A61K 38/07; A61K 38/08; A61K 8/64; A61K 8/645
USPC ..................... 514/1.1, 18.6, 18.8, 21.8, 21.9; 530/300, 331; 424/59, 70.14
See application file for complete search history.

(56) References Cited

U.S. PATENT DOCUMENTS

| | | | |
|---|---|---|---|
| 5,516,507 | A | 5/1996 | N'Guyen et al. |
| 7,220,417 | B2 | 5/2007 | Nizard et al. |
| 2004/0018983 | A1 | 1/2004 | Rice et al. |
| 2004/0136945 | A1 | 7/2004 | Nizard et al. |
| 2005/0282747 | A1 | 12/2005 | Clark et al. |
| 2007/0274937 | A1 | 11/2007 | Dal Farra et al. |
| 2008/0076718 | A1 | 3/2008 | Reboud-Ravaux et al. |
| 2009/0041866 | A1 | 2/2009 | Miyata |
| 2009/0196837 | A1 | 8/2009 | Msika et al. |

FOREIGN PATENT DOCUMENTS

| | | |
|---|---|---|
| FR | 2822701 | 10/2002 |
| FR | 2898808 | 9/2007 |
| FR | 2904552 | 2/2008 |
| FR | 2915378 | 10/2008 |
| FR | 2915379 | 10/2008 |
| FR | 2915380 | 10/2008 |
| FR | 2915381 | 10/2008 |
| FR | 2915382 | 10/2008 |
| FR | 2915383 | 10/2008 |
| FR | 2915384 | 10/2008 |
| WO | 02/080876 | 10/2002 |
| WO | 2005/061530 | 7/2005 |

(Continued)

OTHER PUBLICATIONS

WO 2008/009709 machine translation, pp. 1-5. Accessed Oct. 28, 2013. WO document printed on Jan. 24, 2008.*

(Continued)

*Primary Examiner* — Julie Ha
(74) *Attorney, Agent, or Firm* — Thompson Hine, L.L.P.

(57) ABSTRACT

A peptidic hydrolyzate enriched in bioactive peptides is disclosed that is a proteasome activator. Cosmetic and pharmaceutical compositions are disclosed that include the peptidic hydrolyzate enriched in bioactive peptides in a physiologically acceptable medium. Also disclosed are methods for depigmenting, lightening and/or whitening the skin and treating hyperpigmentation blemishes as well as cutaneous signs due to photo-aging by administering the cosmetic compositions or pharmaceutical compositions.

15 Claims, 2 Drawing Sheets

(56) References Cited

FOREIGN PATENT DOCUMENTS

| WO | 2005/107697 | 11/2005 |
|---|---|---|
| WO | 2006/105811 | 10/2006 |
| WO | 2007/131774 | 11/2007 |
| WO | 2008/009709 | 1/2008 |
| WO | 2008/015343 | 2/2008 |

OTHER PUBLICATIONS

PCT, International Search Report, International Application No. PCT/FR2010/000325 (mailed Jul. 22, 2010; published Oct. 28, 2010).
Bulteau, A-L. et al., "Algae Extract-Mediated Stimulation and Protection of Proteasome Activity Within Human Keratinocytes Exposed to UVA and UVB Irradiation," *Antioxidants & Redox Signaling*, vol. 8, Nos. 1 & 2, pp. 136-143 (2006).
Coux, O. et al., "Structure and Functions of the 20S and 26S Proteasomes," *Ann. Rev. Biochem.*, 65, pp. 801-847 (1996).
Glickman, M. et al., "Purification and Characterization of Proteasomes from *Saccharomyces cerevisiae*," *Current Protocols in Protein Science*, published by John Wiley & Sons, Inc., pp. 21.5.1 through 21.5.17 (2001).
Glickman, M.H. et al., "The Ubiquitin-Proteasome Proteolytic Pathway: Destruction for the Safe of Construction," *Physiol. Rev.*, 82, pp. 373-428 (2002).
Machine generated English translation of WO 2008/009709 A1 (Jan. 24, 2008).
Berendsen, A Glimpse of the Holy Grail?, Science, 282, pp. 642-643 (1998).
Bradley et al., Limits of Cooperativity in a Structurally Modular Protein: Response of the Notch Ankyrin Domain to Analogous Alanine Substitutions in Each Repeat, J. Mol. Biol., 324, pp. 373-386 (2002).
Merck Manual Home Edition, Effects of Aging on the Skin (1 page) (Oct. 2006).
Merck Manual Professional, Chronic Effects of Sunlight (2 pages) (Aug. 2007).
Ngo et al., Computational Complexity, Protein Structure Protection, and the Levinthal Paradox, pp. 491-494 (1994).
Rudinger, Peptide Hormones, J.A. Parsons, Ed., p. 1-7 (1976).
SIGMA, Designing Custom Peptides (2 pages) (2004).
Voet et al., Biochemistry, John Wiley & Sons Inc., pp. 235-241 (1995).
Machine translation of FR 2915384, pp. 1-27 (Oct. 31, 2008).
PCT, International Preliminary Report on Patentability, International Application No. PCT/FR2010/000325 (Nov. 1, 2011).
Chondrogianni, N. et al., "Proteasome dysfunction in mammalian aging: Steps and factors involved," *Experimental Gerontology*, 40, pp. 931-938 (2005).
Harman, D., "Aging: A Theory Based on Free Radical and Radiation Chemistry," *J. Gerontol.*, 11 (3), pp. 298-300 (1956).
Kullmann, W., "Proteases as Catalysts for Enzymic Synthesis of Opioid Peptides," *The Journal of Biological Chemistry*, vol. 255, No. 17, pp. 8234-8238 (Sep. 10, 1980).
Petropoulos, I. et al., "Increase of Oxidatively Modified Protein is Associated With a Decrease of Proteasome Activity and Content in Aging Epidermal Cells," *J. Gerontol. A. Biol. Sci.*, vol. 55A, No. 5, pp. B220-B227 (2000).

* cited by examiner

Figure 1: HPLC chromatogram of a corn hydrolysate

Figure 2: HPLC chromatogram of a pea hydrolysate

Figure 3: HPLC chromatogram of a rice hydrolysate

Figure 4: HPLC chromatogram of a saccharomyces hydrolysate

SEQUENCE LISTING

```
<160> NUMBER OF SEQ ID NOS: 5

<210> SEQ ID NO 1
<211> LENGTH: 5
<212> TYPE: PRT
<213> ORGANISM: Zea mays
<220> FEATURE:
<221> NAME/KEY: MISC_FEATURE
<223> OTHER INFORMATION: The sequence also may be obtained from Pisum
      sativum, Oryza sativa, or Saccharomyces cerevisiae.
```

```
<400> SEQUENCE: 1

Arg Asp Cys Arg Arg
1               5

<210> SEQ ID NO 2
<211> LENGTH: 5
<212> TYPE: PRT
<213> ORGANISM: Zea mays
<220> FEATURE:
<221> NAME/KEY: MISC_FEATURE
<223> OTHER INFORMATION: The sequence also may be obtained from Pisum
      sativum, Oryza sativa, or Saccharomyces cerevisiae.

<400> SEQUENCE: 2

Asn Asp Cys Arg Lys
1               5

<210> SEQ ID NO 3
<211> LENGTH: 4
<212> TYPE: PRT
<213> ORGANISM: Zea mays
<220> FEATURE:
<221> NAME/KEY: MISC_FEATURE
<223> OTHER INFORMATION: The sequence also may be obtained from Pisum
      sativum, Oryza sativa, or Saccharomyces cerevisiae.

<400> SEQUENCE: 3

Asp Cys Arg His
1

<210> SEQ ID NO 4
<211> LENGTH: 4
<212> TYPE: PRT
<213> ORGANISM: Zea mays
<220> FEATURE:
<221> NAME/KEY: MISC_FEATURE
<223> OTHER INFORMATION: The sequence also may be obtained from Pisum
      sativum, Oryza sativa, or Saccharomyces cerevisiae.

<400> SEQUENCE: 4

Val Asp Cys Arg
1

<210> SEQ ID NO 5
<211> LENGTH: 3
<212> TYPE: PRT
<213> ORGANISM: Zea mays
<220> FEATURE:
<221> NAME/KEY: MISC_FEATURE
<223> OTHER INFORMATION: The sequence also may be obtained from Pisum
      sativum, Oryza sativa, or Saccharomyces cerevisiae.

<400> SEQUENCE: 5

Asp Cys Arg
1
```

PROTEASOME-ACTIVATING LIGHTENING PEPTIDIC HYDROLYZATES AND COMPOSITIONS CONTAINING THEM

The present invention relates to the field of depigmenting active principles and their uses in cosmetics, in particular. More particularly, the present invention relates to a peptidic hydrolyzate enriched in bioactive peptides, said hydrolyzate being a proteasome activator, as well as its applications in cosmetics and/or pharmaceuticals as a lightening, depigmenting and/or whitening agent. Said hydrolyzate also enables the cutaneous signs of a hyperpigmentary nature due to photo-aging, as well as hyperpigmentation blemishes of various origins to be prevented and/or treated.

In humans, the color of the hair and the skin is connected to individual factors (ethnic origin, sex, age, etc.) and to environmental factors (particularly the seasons of the year, living area, etc.). It is mainly determined by the nature and concentration of melanin produced by the melanocytes. Melanin has the property of protecting skin cells from the deleterious effects of UV radiation and slowing down cutaneous photo-aging. Melanocytes are specialized cells that, through particular organelles called melanosomes, synthesize melanin. Melanin synthesis, or melanogenesis, is a complex process whose precise mechanisms have still not been clarified and that schematically involves the following steps:

Tyrosine→Dopa→Dopaquinone→Dopachrome→Melanin.

This melanin in fact plays a fundamental role in determining skin color. Melanin is synthesized by large dendritic cells: melanocytes, cells located in the basal layer of the epidermis. Melanin exists in two different forms: pheomelanin, a yellow pigment, and eumelanin, a black pigment. It is the different proportions and size of these pigments, without forgetting carotenoids and blood micro-circulation, that give the skin its great color diversity.

The production of melanin, as well as its transport, is regulated by different factors such as, for example, UV radiation, hormones or chemical products. Thus, an increase in UV radiation exposure causes pigments to be synthesized and results in darkening of the skin. Disturbances in this pigmentation, more or less benign, may appear. These disturbances are manifested in, for example, freckles, beauty marks, diffuse blemishes such as pregnancy blemishes, chloasma and melasma, as well as other hyperpigmentary disorders such as, for example, lentigo. Other hyperpigmentation blemishes may be due, for example, to poor cicatrization, particularly in individuals with a dark phenotype, or else they may be due to the use of photosensitizing medications, etc. But aging may itself also modulate skin pigmentation. Thus, some persons may see blotches appear on the skin, that are more or less dark or colored, conferring heterogeneous coloration zones forming senescence blotches or else epheledes. Lastly, in some Asian or else African populations, lightening cosmetic treatment is desired to obtain a clear and uniform complexion.

The use of melanin synthesis inhibitors or regulators, as well as any other depigmenting and/or whitening product, is thus of particular interest in cosmetology and/or dermatology. This use is not only of interest when true skin depigmentation is desired, as in the case of whitening highly pigmented skin or else inhibiting hyperpigmented skin zones resulting in an unsightly skin appearance; it is also of interest in certain applications aiming to lighten the complexion, to give the skin luminosity or else to give the surface tissues luster.

To date, many molecules have been proposed that are more or less effective. Among these molecules phenol derivatives such as hydroquinone and resorcinol, that inhibit a series of reactions of L-tyrosine conversion into melanin by inhibiting tyrosinase activity may be cited (Takano, 1984). L-ascorbic acid and its derivatives, magnesium ascorbyl acetate, kojic acid or else lactic acid may also be cited.

But most products currently on the market are toxic and/or do not present sufficient effectiveness. For example, hydroquinone is irritating and cytotoxic to melanocytes. For example, kojic acid is not stable in solution, etc. Therefore, a need exists for a novel whitening agent that would not present the disadvantages of existing agents but would be just as effective. This is why other pathways have been explored in order to find a novel depigmenting agent acting on both the tyrosinase enzyme and on melanin.

Surprisingly, the Applicant has discovered that a peptidic hydrolyzate enriched in bioactive peptides, said hydrolyzate being a proteasome activator, may be utilized as a whitening agent and presented good depigmenting activity without necessarily being toxic.

The ubiquitin-proteasome pathway plays a fundamental role in a very large number of biological processes. In fact, the degradation mechanisms of proteins by proteasome are involved in significant cellular mechanisms such as DNA repair, gene expression control, cell cycle progression regulation, neosynthesized protein quality control, apoptosis or immune response (Glickman and Ciechanover, 2002).

The proteasome present in human cells is a very large size multi-proteinic complex present in the cytoplasm and nucleus. The purified forms of proteasome comprise 2 large subunits; on the one hand, a proteolytic core called 20S proteasome and, on the other hand, a 19S regulating complex that is bound to each of the two ends of the 20S proteasome (Coux et al., 1996; Glickman and Coux, 2001). The 20S proteasome is a particle in a hollow cylinder shape, composed of 28 alpha and beta subunits, distributed in 4 heptameric rings. Peptidase activities are present on the inner surface of the cylinder and affect one another allosterically. Three proteolytic activities ("trypsin, chymotrypsin and caspase-like") have been associated with the 20S proteasome and help destroy proteins into inactive peptides with 3 to 20 amino acids. In addition to the 20S proteasome, the 26S proteasome comprises the 19S regulating complex of 0.7 MDa, constituted of approximately 20 subunits. Recent immunopurification studies have shown that other proteins may be combined with 20S and 19S proteasome (for example the 11S regulating complex).

In view of the diversity of cellular processes controlled via protein degradation, it is not surprising to observe that ubiquitin-proteasome pathway alterations are at the origin of, or closely connected to, several genetic diseases and numerous human pathologies such as colorectal cancers, lymphoma, inflammatory syndromes, or neurodegenerative diseases such as Parkinson's disease or Alzheimer's disease.

Many works have been carried out over these last few years on the role of proteasome in aging of the skin. One of the pathways explored recently turned to proteasome and its action on the degradation of proteins involved in melanogenesis. Experiments have shown that degradation of the tyrosinase enzyme by proteasome was activated by an algae extract on human melanocytes (Bulteau et al. Antioxid. Redox Signal; 2006, 1-2:136-143).

A composition comprising an extract of silybin, Bletilla striata and Iris sanguinea capable of increasing proteasome activity and enabling an effect on skin pigmentation was disclosed in a (U.S. Ser. No. 12/088,919).

This is how the Applicant discovered that a peptidic hydrolyzate enriched in bioactive peptides was capable of activating proteasome and thus may depigment, lighten or even whiten the skin and epithelial appendages.

Consequently, the first object of the present invention is a proteasome activating peptidic hydrolyzate, enriched in bioactive peptides, with a molecular weight of less than 6 kDa comprising from 3 to 5 amino acids, each bioactive peptide comprising at least one aspartic acid residue, one cysteine residue and an arginine residue.

The second object of the present invention is a cosmetic composition comprising said enriched peptidic hydrolyzate as an active principle.

In addition, the third object of the present invention is the use of a cosmetic composition comprising said peptidic hydrolyzate to improve the degradation by proteasome of damaged proteins and thus depigment the skin and/or epithelial appendages, and prevent and/or treat hyperpigmentation blemishes.

Lastly, the fourth object of the present invention is a method of cosmetic treatment of the skin or epithelial appendages to be treated by using a composition containing said enriched peptidic hydrolyzate.

The first object of the present invention is a proteasome activating peptidic hydrolyzate, enriched in bioactive peptides, with a molecular weight of less than 6 kDa, comprising from 3 to 5 amino acids, each bioactive peptide comprising at least one aspartic acid residue, one cysteine residue and an arginine residue.

"Peptidic hydrolyzate" is understood to refer to a mixture of compounds predominantly represented by peptides or oligopeptides.

"Bioactive peptides" is understood to refer to a protein fragment composed of a linkage of at least 3 amino acids interconnected by modified or unmodified peptide linkages and that presents an activity as a proteasome activator. Present in inactive form in the proteins, they become active after the proteins are hydrolyzed.

Said enriched peptidic hydrolyzate according to the invention is characterized in that it is a proteasome activator.

"Proteasome-activating" peptidic hydrolyzate (and/or bioactive peptides) is or are understood to refer to any biologically active peptidic hydrolyzate or peptide or derivative capable of increasing proteasome activity, either by increasing the protein synthesis of proteasome subunits (by direct or indirect modulation of the gene expression) or by other biological processes such as stabilizing the subunits constituting the proteasome or else stabilizing RNA messenger transcripts.

The enriched peptidic hydrolyzate according to the invention is characterized in that it activates degradation by proteasome of damaged proteins. "Damaged proteins" is understood to refer to proteins that have undergone oxidation reactions due to reactive species of oxygen (free radicals), glycated or conjugated proteins with products issued from lipid peroxidation, etc.

Preferentially, the peptidic hydrolyzate is enriched in bioactive peptides of general formula (I):

$X_1$-[Asp, Cys, Arg]-$X_2$ in which, $X_1$ is an asparagine, a lysine, an aspartate, a valine, an arginine, or is absent;

$X_2$ is a histidine, a lysine, an arginine, or is absent.

Preferentially, the peptidic hydrolyzate is rich in bioactive peptides of the following formula:

Arg-Asp-Cys-Arg-Arg (SEQ ID NO: 1)

Asn-Asp-Cys-Arg-Lys (SEQ ID NO: 2)

Asp-Cys-Arg-His (SEQ ID NO: 3)

Val-Asp-Cys-Arg (SEQ ID NO: 4)

Asp-Cys-Arg. (SEQ ID NO: 5)

In fact, these peptides have been identified as being particularly active as proteasome activators and thus present a particular interest as lightening agents.

The enriched peptidic hydrolyzate according to the invention may be obtained from various protein sources, whether of animal or plant origin. According to a first embodiment, the enriched peptidic hydrolyzate is from the hydrolysis of plants chosen from among corn (*Zea mayz* L.), pea (*Pisum sativum*), or rice (*Oryza sativa* L.). Preferably, the plants used are not subjected to prior fermentation. In a second mode of embodiment, the enriched peptidic hydrolyzate is from the hydrolysis of yeasts from the *Saccharomyces* genus, and more particularly from the *Saccharomyces cerevisiae* species.

Thus, the invention may be carried out by using the seeds from one of many plants of the *Zea* genus and preferentially the *Zea mays* L species. According to the invention, the plant material utilized will be the seed and, preferentially, the hull of the seed was removed by a hulling step.

The invention may also be carried out by utilizing one of many plants from the pea family (Fabaceae). For example, plants from the pea species *Pisum sativum* L will be used. The term pea also designates the seed, itself rich in proteins (25%).

Plants from the rice family (Poaceae), particularly those from the *Oryza* genus and more preferentially the *Oryza sativa* L species may be used to carry out the hydrolyzate according to the invention. The plant material utilized will be the seed and, preferentially, the hull of the seed was removed by a hulling step.

Lastly, the invention may also be carried out by utilizing yeasts of the *Saccharomyces* genus; and preferentially yeasts of the *Saccharomyces cerevisiae* species.

Any extraction or purification method known to the person skilled in the art may be utilized in order to prepare the hydrolyzate according to the invention.

In a first step, the seeds, or a specific part of the plant (leaves, tubers, roots, etc.) are milled by using a plant mill. The powder thus obtained may subsequently be de-fatted by using a conventional organic solvent (such as for example an alcohol, hexane or acetone).

With yeasts, in a first step, the yeasts are cultured conventionally in a suitable medium for their development, preferably in the presence of lactose. The yeasts are harvested by centrifugation and then suspended in a buffer solution, preferentially a phosphate buffer. In a second step, the cells are burst by using a French press or by using a ball mill, the majority of insoluble membrane components being separated by centrifugation or filtration.

Then proteins are extracted according to the modified conventional method (Osborne, 1924); the plant ground material or yeast lysate is suspended in an alkaline solution containing an adsorbent product of the insoluble polyvinylpolypyrrolidone (PVPP) type (0.01-20%); In fact, it was observed that subsequent hydrolysis and purification operations were facilitated by this means. In particular, the concentration of phenolic type substances, interacting with proteins, is markedly reduced.

The soluble fraction, containing proteins, carbohydrates and possibly lipids, is collected after the centrifugation and filtration steps. This crude solution is then hydrolyzed under controlled conditions to generate soluble peptides. Hydrolysis is defined as being a chemical reaction involving cleavage of a molecule by water, this reaction may be done in neutral, acidic or basic medium. According to the invention, hydrolysis is carried out chemically and/or advantageously by proteolytic enzymes. The use of plant origin endoproteases (papain, bromelin, ficin) and microorganisms (*Aspergillus, Rhizopus, Bacillus,* etc.) may then be cited. The hydrolysis conditions are chosen to promote bioactive peptide enrichment.

For the same reasons as above, i.e., the elimination of polyphenolic substances, a quantity of polyvinylpolypyrrolidone is added to the reaction medium during this controlled hydrolysis step. After filtration, allowing the enzymes and polymers to be eliminated, a first filtrate is obtained.

The hydrolyzate obtained at this stage may be purified again in order to select the low molecular weight fractions, preferentially lower than 6kDa and the peptides generated according to their nature. Purification is advantageously carried out by successive ultrafiltration steps through filters of decreasing porosity, by conserving the filtrates at each step and/or by a chromatographic type method, in order to specifically enrich the hydrolyzate in bioactive peptides.

Then the invention carries out a phase of dilution in water or in any mixture containing water, and then sterilization by ultrafiltration in order to obtain an enriched peptidic hydrolyzate characterized by a protein content from 0.5 to 5.5 g/l. This enriched peptidic hydrolyzate corresponds to the most purified form of the active principle according to the invention.

The peptidic hydrolyzate obtained according to the invention is qualitatively and quantitatively analyzed in high pressure liquid chromatography (HPLC), enabling the proteins having molecular weights from 0.2 to 25 kDa (according to a gradient of appropriate solvents) to be analyzed. The different peptidic fractions that could be isolated are then analyzed for their biological effectiveness. These diverse fractions are then analyzed by mass spectrometry in order to specifically identify the amino acid content of the peptides from each peak. A sequencing analysis was also carried out, to determine the peptidic sequence of the bioactive peptides.

Finally, the enriched peptidic hydrolyzate obtained is composed of peptides with a molecular weight of less than 6 kDa, and is enriched in bioactive peptides from 3 to 5 amino acids, comprising at least one aspartic acid residue, one cysteine residue and one arginine residue.

This peptidic hydrolyzate according to the invention, enriched in bioactive peptides may also be used as a medication.

The second object of the present invention refers to a cosmetic composition comprising as the active principle the peptidic hydrolyzate enriched in bioactive peptides such as described previously.

Preferably, the compositions according to the invention are present in a form suitable for topical application comprising a cosmetically acceptable medium. "Cosmetically acceptable" is understood to refer to media that are suitable for a use in contact with the skin or with human epithelial appendages, without risk of toxicity, incompatibility, instability, allergic response or other secondary effects. Preferentially, said peptidic hydrolyzate is present in the composition in a quantity representing from 0.0001% to 20% of the total weight of the composition, and preferentially in a quantity representing from 0.05% to 5% of the total weight of the composition.

In the compositions according to the invention, the peptidic hydrolyzate enriched in bioactive peptides is solubilized in one or more solvents, such as water, glycerol, ethanol, propylene glycol, butylene glycol, dipropylene glycol, ethoxylated or propoxylated diglycols, cyclic polyols, white petroleum jelly, vegetable oil or any mixture of these solvents.

According to still another advantageous embodiment, the peptidic hydrolyzate according to the invention is solubilized in a cosmetic or pharmaceutical carrier such as liposomes, or adsorbed on powdery organic polymers, mineral supports such as talcs and bentonites, and more generally solubilized in, or fixed on, any physiologically acceptable carrier.

The compositions intended to be applied on the skin may be present in the form of an aqueous or hydroalcoholic solution, water in oil emulsion or oil in water emulsion, microemulsion, aqueous or anhydrous gel, serum, or else vesicle dispersion, patch, cream, spray, ointment, pomade, lotions, colloid, solution, suspension or other forms. The compositions may also be applied onto the epithelial appendages in the form of shampoo, hair tint or mascara to be applied by brush or comb, in particular onto the eyelashes, eyebrows or hair, or else nail treatment such as nail polish.

In a particular embodiment, the composition according to the invention also contains at least one other active principle promoting the action of said enriched peptidic hydrolyzate. One may cite, in a non-limiting manner, classes of ingredients presenting activity in the field of lightening agents such as desquamant agents; soothing agents, organic or inorganic photo-protective agents, moisturizing agents; other depigmenting agents, tyrosinase inhibitors; agents stimulating the synthesis of dermal or epidermal macromolecules and/or preventing their degradation; agents stimulating the proliferation of fibroblasts and/or keratinocytes or stimulating keratinocyte differentiation; agents acting on the energy metabolism of cells; Other depigmenting peptides, plant hydrolyzates, anti-aging agents, as well as their mixtures. In addition, additives such as thickening agents, emulsifiers, humectants, emollients, fragrances, antioxidants, film-forming agents, chelating agents, sequestering agents, conditioners, etc., may be added to the composition.

In all cases, the person skilled in the art will make sure that these adjuvants as well as their proportions are chosen so as to not harm the desired advantageous properties of the composition according to the invention. These adjuvants may, for example, be comprised between 0.01 to 20% of the total weight of the composition. When the composition of the invention is an emulsion, the fatty phase may represent from 5 to 80% by weight and preferably from 5 to 50% by weight with relation to the total weight of the composition. The emulsifiers and co-emulsifiers utilized in the composition will be chosen from among those conventionally utilized in the field under consideration. For example, they may be utilized in a proportion going from 0.3 to 30% by weight with relation to the total weight of the composition.

Lastly, the composition as described enables the proteasome activity to be increased and improves degradation by proteasome of damaged proteins involved in melanogenesis.

A third object of the invention relates to the use of a cosmetic composition comprising said enriched peptidic hydrolyzate and a cosmetically acceptable medium to depigment, lighten and/or whiten the skin.

The composition according to the invention also prevents and/or treats hyperpigmentation blemishes such as melasma, chloasma, actinic lentigo, solar lentigo, ephelides, accidental hyperpigmentation blemishes and post-scarring hyperpigmentation blemishes.

Another object of the invention relates to the use of a composition comprising said peptidic compound to treat and/or prevent skin signs of a hyperpigmentary nature due to photo-aging. "Photo-aging" is understood to refer to the premature aging of the skin caused by prolonged and cumulative sun exposure.

Lastly, another object of the invention refers to the use of a cosmetic composition according to the invention to increase the activity of proteasome and improve degradation by proteasome of damaged proteins involved in melanogenesis.

A final object of the present invention relates to a cosmetic treatment method characterized in that a composition comprising an effective quantity of the peptidic hydrolyzate according to the invention is applied topically to the skin or epithelial appendages to be treated to depigment, lighten and/or whiten the skin or epithelial appendages. In addition, this cosmetic treatment method is also intended to prevent and/or treat the cutaneous signs of a hyperpigmentary nature due to photo-aging.

The following examples describe and demonstrate the effectiveness of peptidic compounds as described according to the invention but should not be interpreted as a limitation of the present invention.

EXAMPLE 1

Preparation of a Peptidic Hydrolyzate from Corn Germ Cake (*Zea Mays* L.)

The corn germ cake (*Zea mays* L.) is put in solution in 10 volumes of water in the presence of 2% POLYCLAR® 10 polyvinylpolypyrrolidone (PVPP-insoluble). The mixture is adjusted to a pH of between 6 and 8 with an aqueous solution of sodium hydroxide 1 M.

After adjustment of the pH, papain at 2% is added to the reaction medium. The hydrolysis is obtained after 2 hours of agitation at 55° C. The enzyme is then inactivated by heating the solution to 80° C. for 2 hours. After centrifugation, the supernatant aqueous solution corresponding to a crude corn hydrolyzate is recovered. Specific hydrolysis conditions are chosen so as to enable enrichment in bioactive peptides of 3 to 5 amino acids comprising at least one aspartic acid residue, one cysteine residue and one arginine residue.

The crude hydrolyzate purification process starts by successive filtrations by using Seitz-Orion filter plates of decreasing porosity (up to 0.2 µm) in order to obtain a bright and clear yellow solution, described as hydrolyzate 1.

At this step, the corn hydrolyzate 1 is characterized by a dry extract titrating from 20 to 30 g/kg, a protein level from 20 to 25 g/l and a sugar level from 2 to 5 g/l.

The protein nature of hydrolyzate 1 is demonstrated after electrophoresis analysis on NUPAGE® Bis-Tris Pre-cast (In-vitrogen) polyacrylamide gel. The corn protein hydrolyzate is heated to 70° C. for 10 minutes under reducing denaturing conditions in a NUPAGE® LDS sample preparation buffer. Protein migration is carried out in the NUPAGE® MES migration buffer with the standard SEEBLUE® Plus2 prestained standard as a molecular weight marker. Protein coloration is carried out by using Coomassie Blue R-250 dye. Under these conditions, proteins with a molecular weight of less than 6 kDa are observed.

The hydrolyzate 1 is then purified by eliminating high molecular weight proteins by ultrafiltration by using the PELLICON® 2 Biomax cassette filtration device 5 kDa in order to only retain peptidic nature compounds of less than 5 kDa.

After this final purification, a dilution phase is carried out in order to obtain a peptidic hydrolyzate characterized by a protein level of between 3.5 and 5.5 g/l. This peptidic hydrolyzate enriched in bioactive peptides corresponds to the active principle according to the invention.

This peptidic hydrolyzate is then analyzed by high pressure liquid chromatography (HPLC) by using an HP1100 apparatus run by the ChemStation software. The column used during elution of the hydrolyzate is a NUCLEOSIL® 300-5 C4 MPN (125×4 mn) column, enabling the proteins having molecular weights from 0.2 to 25 kDa to be chromatographed under the following conditions:

Methanol gradient
Uptisphere OPB 125×3 mm column
Solvent A: HPLC grade water containing 0.1% heptaflurobutyric acid (HFBA)
Solvent B: HPLC grade methanol containing 0.1% heptaflurobutyric acid (HFBA)
Gradient: 100% to 15% solvent A in 35 min.

Figure 1:
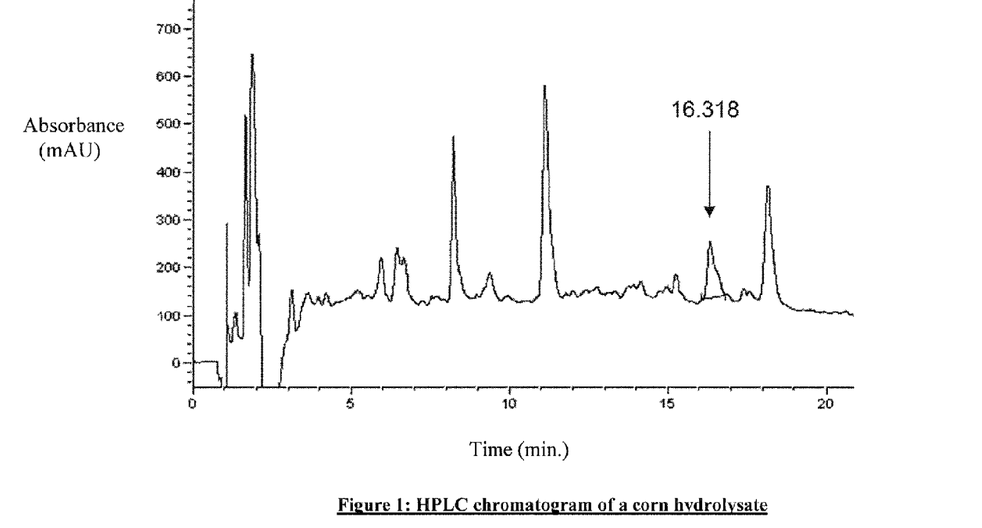
FIG. 1 represents a chromatogram example obtained by HPLC, with demonstration of the peak corresponding to the bioactive peptide in a corn hydrolyzate.

An example of a chromatogram obtained by HPLC (high pressure liquid chromatography), with demonstration of the peak corresponding to the bioactive peptides is given in FIG. 1.

These diverse fractions are then analyzed by mass spectrometry in order to specifically identify the amino acid content of the peptides from each peak. A sequencing analysis was also carried out, to determine the peptidic sequence of the bioactive peptides.

EXAMPLE 2

Preparation of a Peptidic Hydrolyzate Enriched in Bioactive Peptides from Peas (*Pisum Sativum* L.)

The peptidic hydrolyzate is obtained from a plant extract of the *Pisum sativum* L species. Of course, the extract may be prepared from plants of at least any one of the many varieties and species belonging to the *Pisum* genus.

In a first step, 1 kg of hulled peas is de-fatted by the action of an organic solvent: hexane.

The pea flour thus obtained is put in solution in 10 volumes of water in the presence of 2% POLYCLAR® polyvinylpolypyrrolidone (PVPP-insoluble). The mixture is adjusted to a pH of between 6 and 7 with an aqueous solution of sodium hydroxide 1 M.

After adjustment of the pH, FLAVOURZYME® enzymes at 2% is added to the reaction medium. Hydrolysis is obtained after 2 hours of agitation at 50° C. The enzyme is then inactivated by heating the solution to 80° C. for 2 hours. The reaction mixture thus obtained corresponds to the pea extract. Specific hydrolysis conditions are chosen so as to enable enrichment in bioactive peptides of 3 to 5 amino acids comprising at least one aspartic acid residue, one cysteine residue and one arginine residue.

The purification process starts by successive filtrations by using Seitz-Orion filter plates of decreasing porosity (up to 0.2 μm) in order to obtain a bright and clear solution. In this step, the pea hydrolyzate is characterized by a dry extract titrating from 70-80 g/kg, a protein level of 55-65 g/l, a sugar level of 2-5 g/l and a polyphenol level of 1-3 g/l.

The protein nature of this hydrolyzate is demonstrated by electrophoresis on polyacrylamide gel. For this analysis, NUPAGE® Bis-Tris Pre-cast (Invitrogen) gels are utilized. The pea peptidic hydrolyzate is heated to 70° C. for 10 minutes under reducing denaturing conditions in a NUPAGE® LDS sample preparation buffer. Protein migration is carried out by using the NUPAGE® MES migration buffer with the standard SEEBLUE® Plus2 pre-stained standard as a molecular weight marker. Protein coloration is carried out by using Coomassie Blue R-250 dye. Under these conditions, 2 large protein families are observed: The 1st family corresponds to proteins of molecular weight from 20 to 25 kDa and the last family to proteins of molecular weight of less than 5 kDa.

This solution is then purified by eliminating proteins of molecular weight greater than 5 kDa by using tangential flow filtration. To do this, the pea hydrolyzate is pumped under pressure through a PELLICON® support equipped with a PELLICON® 2 Biomax cassette filtration device 30 kDa. This 1st filtrate is recovered to then be filtered through another PELLICON® 2 Biomax cassette filtration device 5 kDa. At the end of purification, a bright and clear yellow-beige pea peptidic hydrolyzate is obtained. It is characterized by a dry extract of 50 to 55 g/kg, a protein content of 50 to 52 g/l.

This solution is then analyzed by high pressure liquid chromatography (HPLC) by using an HP1100 apparatus run by the CHEMSTATION® software. The column utilized during elution of the pea extract is a NUCLEOSIL® 300-5 C4 MPN (125×4 mn) column. This column enables proteins having molecular weights of 0.2 to 25 kDa to be chromatographed (according to a suitable solvent gradient, identical to example 1). Under these chromatographic conditions, several peptidic fractions could be isolated.

Figure 2:
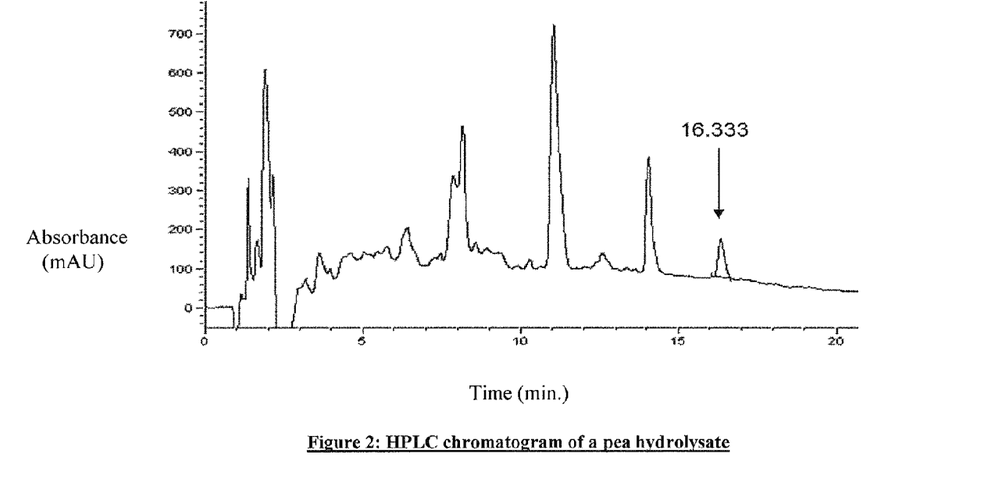
FIG. 2 represents a chromatogram example obtained by HPLC, with demonstration of the peak corresponding to the bioactive peptide in a pea hydrolyzate.
Figure 3:
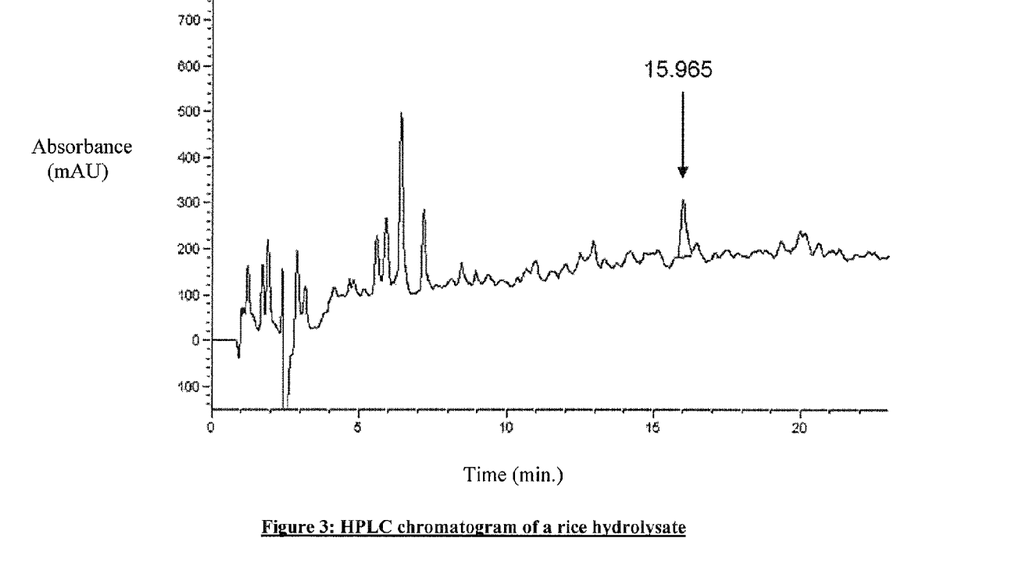
FIG. 3 represents a chromatogram example obtained by HPLC, with demonstration of the peak corresponding to the bioactive peptide in a rice hydrolyzate.

These diverse fractions are then analyzed by mass spectrometry in order to specifically identify the amino acid content of the peptides from each peak. A sequencing analysis was also carried out, to determine the peptidic sequence of the bioactive peptides. An example of a chromatogram obtained by HPLC (high pressure liquid chromatography), with demonstration of the peak corresponding to the bioactive peptides is given in FIG. 2.

The determination of the composition in amino acids of the active principle according to the invention was also carried out. This is achieved after acid hydrolysis and identification by high pressure liquid chromatography by using pre-derivation with PICT (phenylisothiocyanate).

EXAMPLE 3

Preparation of a Peptidic Hydrolyzate Enriched in Bioactive Peptides from *Saccharomyces Cerevisiae* Yeasts The peptidic hydrolyzate may be obtained from an extract of yeasts from the *Saccharomyces cerevisiae* species. The yeasts are cultivated in a suitable medium for their development, preferably in the presence of lactose, and then centrifuged to recover a biomass. The *Saccharomyces* biomass is put in solution in 10 volumes of water in the presence of 2% polyvinylpyrrolidone (POLYCLAR® 10 polyvinylpolypyrrolidone-insoluble) and 0.2% activated carbon. The mixture is adjusted to a pH of between 6 and 7.5 with an aqueous solution of sodium hydroxide 1 M.

After adjustment of the pH, 2% papain is added to the reaction medium. Hydrolysis is obtained after 2 hours of agitation at 55° C. The enzyme is then inactivated by heating the solution to 80° C. for 2 hours. After centrifugation, the reaction mixture corresponding to the *Saccharomyces* extract is then obtained. Specific hydrolysis conditions are chosen so as to enable enrichment in bioactive peptides of 3 to 5 amino acids comprising at least one aspartic acid residue, one cysteine residue and one arginine residue.

The purification process starts by successive filtrations by using Seitz-Orion filter plates of decreasing porosity (up to 0.2 μm) in order to obtain a bright and clear solution. At this step, the *Saccharomyces* extract is characterized by a dry extract from 25 to 35 g/kg, a protein level from 10 to 15 g/l and a sugar level from 5-10 g/l.

The protein nature of this extract is demonstrated by electrophoresis on polyacrylamide gel. For this analysis, NUPAGE® Bis-Tris Pre-cast (Invitrogen) gels are utilized. The peptidic hydrolyzate is heated to 70° C. for 10 minutes under reducing denaturing conditions in a NUPAGE® LDS sample preparation buffer. A NUPAGE® Antioxidant solution is added into the inner tank (cathode) to prevent the reduced proteins from reoxidizing during electrophoresis. Protein migration is carried out by using the NUPAGE® MES migration buffer with the standard SEEBLUE® Plus2 pre-stained standard as a molecular weight marker. Protein coloration is carried out by using Coomassie Blue R-250 dye. Under these conditions, 3 large protein families are observed: The 1st family corresponds to proteins of molecular weight greater than 75 kDa, the 2nd family to proteins from 20 to 25 kDa and the last family to proteins of molecular weight less than 5 kDa.

This solution is then purified by eliminating proteins of molecular weight greater than 5 kDa by using tangential flow filtration. To do this, the *Saccharomyces* peptidic hydrolyzate is pumped under pressure through a PELLICON® support equipped with a PELLICON® 2 Biomax cassette filtration device 50 kDa. This 1st filtrate is recovered to then be filtered through a second PELLICON® 2 Biomax cassette filtration device 10 kDa. A second filtrate is then recovered that is again eluted through a last PELLICON® 2 Biomax cassette filtration device 5 kDa. At the end of purification, a beige, bright and clear *Saccharomyces* plant extract is obtained. It is characterized by a dry extract from 35 to 45 g/kg, a protein content from 30 to 40 g/l.

This solution is then analyzed by high pressure liquid chromatography (HPLC) by using an HP1100 apparatus run by the CHEMSTATION® software. The column utilized during elution of the *Saccharomyces* hydrolyzate is a NUCLEOSIL® 300-5 C4 MPN (125×4 mn) column. This column enables proteins having molecular weights of 0.2 to 25 kDa to be chromatographed (according to a suitable solvent gradient, identical to example 1). Under these chromatographic conditions, several peptidic fractions were isolated.

Figure 4:
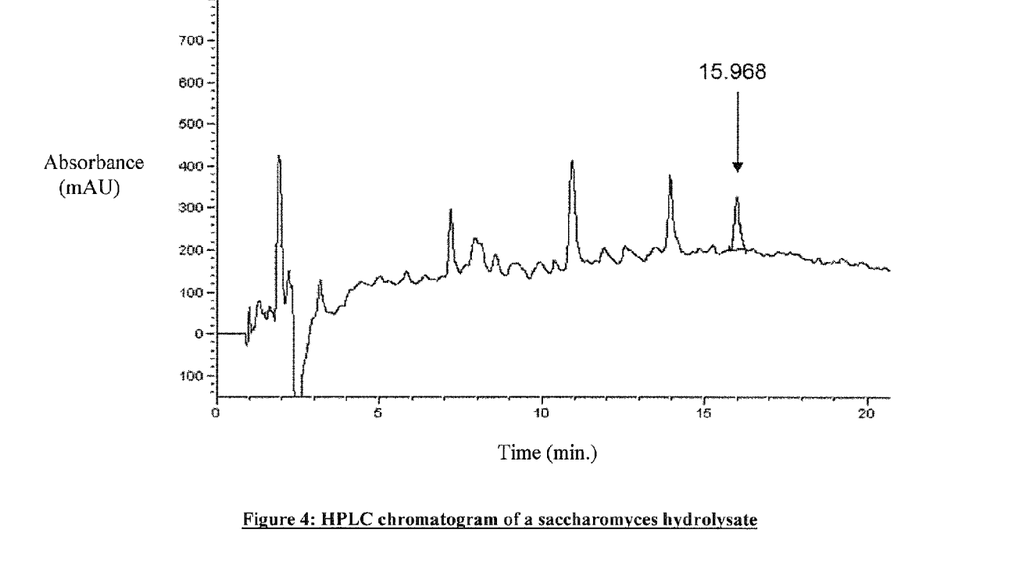
FIG. 4 represents a chromatogram example obtained by HPLC, with demonstration of the peak corresponding to the bioactive peptide in a *Saccharomyces cerevisiae* hydrolyzate.

These diverse fractions are then analyzed by mass spectrometry in order to specifically identify the amino acid content of the peptides from each peak. A sequencing analysis was also carried out, to determine the peptidic sequence of the bioactive peptides. An example of a chromatogram obtained by HPLC (high pressure liquid chromatography), with demonstration of the peak corresponding to the bioactive peptides is given in FIG. 4.

The determination of the composition in amino acids of the active principle according to the invention was also carried out. This is achieved after acid hydrolysis and identification by high pressure liquid chromatography by using pre-derivation with PICT (phenylisothiocyanate).

EXAMPLE 4

Demonstration of the Depigmenting Effect of a Yeast Peptidic Hydrolyzate Enriched in Bioactive Peptides, by Ex Vivo Tests The depigmenting activity of a yeast hydrolyzate enriched in bioactive peptides carried out according to the invention was demonstrated on a skin sample.

6 mm diameter biopsies are taken from human skin samples. These biopsies are maintained in ex vivo survival in the presence of a specific medium (DMEM 1 g/L, HAMF12, SVF and antibiotics) on inserts deposited in 6-well plates. The biopsies are then pretreated for 24 hours with the peptidic hydrolyzate at 3% concentration at a rate of 2 applications per day. Other skin samples will not be pretreated with the same hydrolyzate and will be used as the control condition. Subsequently, the biopsies are subjected to UVB irradiation at a rate of 100 mJ/cm$^2$. The pretreated biopsies are treated again for 24 hours with the peptidic hydrolyzate at 3% concentration at a rate of 2 applications per day. After this second treatment, a quantitative evaluation of the quantity of melanin present in the epidermis of skin samples is carried out histologically, with an optical microscope, after staining according to the Fontana-Masson method.

To do this, the skin biopsies are enclosed in paraffin and histological sections with a thickness of 4 μm are made. These sections are then stained by the Fontana-Masson technique: The paraffin is removed from the slides, the slides are hydrated and then treated with a silver ammonium hydroxide solution. After passing two minutes in the microwave, the slides are rinsed, treated with sodium thiosulfate, rinsed again and counterstained with hematoxylin before being dehydrated and mounted under coverslips, thus enabling the melanin present in the epidermis to be seen by optical microscope.

Results:

Before UVB irradiation, untreated skins present a higher pigmentation level compared to skins treated with the yeast peptidic hydrolyzate. After UVB irradiation, the skins treated with said hydrolyzate present a distinctly lower pigmentation level compared to the untreated skins from the control condition. Consequently, these results enable us to conclude that in the absence of UVB irradiation, the yeast peptidic hydrolyzate enriched in bioactive peptides reduces the melanin level by comparison with the untreated skin sample. In addition, melanin synthesis, induced by UVB irradiation, is very distinctly reduced when the skin samples are pretreated with our active principle. Thus, the peptidic hydrolyzate according to the invention enables skin pigmentation to be significantly reduced and inhibits melanin synthesis.

EXAMPLE 5

Depigmenting Cosmetic Composition with Sunscreen

| Trade names | INCI names | Weight percent |
|---|---|---|
| PHASE A | | |
| MONATOV ® 68 | Cetearyl Alcohol (and) Cetearyl Glucoside | 5.00 |
| Isopropyl Palmitate | Isopropyl Palmitate | 7.00 |
| Waglinol 250 | Cetearyl Ethylhexanoate | 3.00 |
| DOW CORNING ® 200 | Dimethicone Polydimethylsiloxane | 0.50 |
| PARSOL ® MCX | Ethylhexyl Methoxycinnamate | 3.00 |
| PARSOL ® 1789 | Butyl Methoxydibenzoylmethane | 1.00 |
| PHENONIP ® | Phenoxyethanol (and) Methylparaben (and) Ethylparaben (and) Butylparaben (and) Propylparaben (and) Isobutylparaben | 0.50 |
| CEGESOFT ® PS6 | Vegetable Oil | 2.00 |
| Jojoba Oil | *Simmondsia Chinensis* (Jojoba) Seed Oil | 5.00 |
| PHASE B | | |
| Demineralized water | Aqua (Water) | qsp |
| Glycerin | Glycerin | 3.00 |
| GLUCAM ® E10 | Methyl Gluceth-10 | 0.50 |
| EDTA Tetrasodium | EDTA | 0.20 |
| PHASE C | | |
| SEPIGEL 305 ® | Polyacrylamide (and) C13-14 Isoparaffin (and) Laureth-7 | 0.35 |
| Lemon Juice | *Citrus medica Limonum* (Lemon) Fruit Extract | 0.23 |
| PHASE D | | |
| Rice peptidic hydrolyzate | | 2.00 |
| Compo parfumante | Parfum (Fragrance) | qsp |
| Colorant | Dye | qsp |

Applicants incorporate by reference the material contained in the accompanying computer readable Sequence Listing entitled "US09-127SequenceListing.txt", which was created on Dec. 30, 2011, and is 1,554 bytes in size, and hereby confirm that the information recorded in the computer readable form is identical to the written sequence listing.

The invention claimed is:

1. A method for depigmenting, lightening and/or whitening the skin or epithelial appendages, the method comprising:

providing a proteasome activating peptidic hydrolyzate comprising bioactive peptides, with a molecular weight of less than 6 kDa, comprising from 3 to 5 amino acids, each bioactive peptide comprising at least one aspartic acid, one cysteine residue, and an arginine residue and corresponding to one of the following sequences:

Arg-Asp-Cys-Arg-Arg; (SEQ ID NO: 1)

Asn-Asp-Cys-Arg-Lys; (SEQ ID NO: 2)

Asp-Cys-Arg-His; (SEQ ID NO: 3)

Val-Asp-Cys-Arg; (SEQ ID NO: 4)

-continued

Asp-Cys-Arg; (SEQ ID NO: 5)
or
and topically applying an effective quantity of said peptidic hydrolyzate to the skin or epithelial appendages to be treated.

2. The method according to claim 1, wherein said peptidic hydrolyzate is from the hydrolysis of plants selected from corn (*Zea mayz* L.), pea (*Pisum sativum*), or rice (*Oryza sativa* L.).

3. The method according to claim 1, wherein said peptidic hydrolyzate is from the hydrolysis of yeasts of the *Saccharomyces* genus.

4. The method according to claim 1, wherein said peptidic hydrolyzate contains between 0.5 and 5.5 g/l of peptidic nature compounds.

5. The method according to claim 1, wherein said peptidic hydrolyzate increases proteasome activity and improves degradation by proteasome of damaged proteins involved in melanogenesis.

6. The method according to claim 1, wherein said peptidic hydrolyzate further treats hyperpigmentation blemishes selected from the group consisting of melasma, chloasma, actinic lentigo, solar lentigo, ephelides, accidental hyperpigmentation blemishes, post-scarring hyperpigmentation blemishes, and combinations thereof.

7. The method according to claim 1, wherein said peptidic hydrolyzate treats cutaneous signs of a hyperpigmentary nature due to photo-aging.

8. The method according to claim 1, wherein said peptidic hydrolyzate is in a cosmetic composition.

9. The method according to claim 3, wherein said peptidic hydrolyzate is from the hydrolysis of yeasts of the *Saccharomyces cerevisiae* species.

10. The method according to claim 8, wherein said peptidic hydrolyzate is present in the cosmetic composition in a quantity representing from 0.0001% to 20% of the total weight of the composition.

11. The method according to claim 8, wherein the cosmetic composition further comprises one or more solvents selected from the group consisting of water, glycerol, ethanol, propylene glycol, butylene glycol, dipropylene glycol, ethoxylated or propoxylated diglycols, cyclic polyols, white petroleum jelly, vegetable oil, and combinations thereof, said peptidic hydrolyzate being solubilized therein.

12. The method according to claim 8, wherein the cosmetic composition further comprises at least one additional active principle promoting the action of said peptidic hydrolyzate.

13. The method according to claim 12, wherein said additional active principle is an agent presenting an activity in the field of lightening agents; soothing agents, organic or inorganic photo-protective agents, moisturizing agent; depigmenting agents, tyrosinase inhibitors, agent stimulating the synthesis of dermal or epidermal macromolecules and/or preventing their degradation; agents stimulating the proliferation of fibroblasts and/or keratinocytes or stimulating keratinocyte differentiation; agents acting on the energy metabolism of cells; depigmenting peptides, plant hydrolyzates, anti-ageing agents, and mixtures thereof.

14. The method according to claim 8, wherein the peptidic hydrolyzate is present in the cosmetic composition in a quantity representing from 0.05% to 5% of the total weight of the composition.

15. The method according to claim 8, wherein said cosmetic composition is in a form suitable for topical application comprising a cosmetically acceptable medium.

* * * * *